US008383393B2

(12) United States Patent
Gumbrecht et al.

(10) Patent No.: US 8,383,393 B2
(45) Date of Patent: Feb. 26, 2013

(54) TITER PLATE, READING DEVICE THEREFOR AND METHOD FOR DETECTING AN ANALYTE, AND USE THEREOF

(75) Inventors: Walter Gumbrecht, Herzogenaurach (DE); Peter Paulicka, Roettenbach (DE)

(73) Assignee: Siemens Aktiengesellschaft, Munich (DE)

( * ) Notice: Subject to any disclaimer, the term of this patent is extended or adjusted under 35 U.S.C. 154(b) by 5 days.

(21) Appl. No.: 12/994,906

(22) PCT Filed: May 22, 2009

(86) PCT No.: PCT/EP2009/056231
§ 371 (c)(1),
(2), (4) Date: Nov. 29, 2010

(87) PCT Pub. No.: WO2009/144173
PCT Pub. Date: Dec. 3, 2009

(65) Prior Publication Data

US 2011/0076690 A1 Mar. 31, 2011

(30) Foreign Application Priority Data

May 30, 2008 (DE) ......................... 10 2008 025 992

(51) Int. Cl.
*C12M 1/34* (2006.01)
*C12Q 1/68* (2006.01)
*G01N 27/00* (2006.01)

(52) U.S. Cl. ................... 435/283.1; 435/6.1; 435/288.2; 435/288.3; 435/288.4; 422/68.1; 422/82.01

(58) Field of Classification Search ........................ None
See application file for complete search history.

(56) References Cited

U.S. PATENT DOCUMENTS

| | | | | |
|---|---|---|---|---|
| 7,070,740 | B1 * | 7/2006 | Matson et al. | 422/552 |
| 7,364,897 | B2 * | 4/2008 | Heaney et al. | 435/287.2 |
| 7,364,899 | B2 | 4/2008 | Kirk et al. | |
| 2001/0051113 | A1 * | 12/2001 | Juncosa et al. | 422/131 |
| 2003/0049866 | A1 * | 3/2003 | Bushway et al. | 436/518 |
| 2003/0077207 | A1 | 4/2003 | Tyndorf et al. | |
| 2004/0029258 | A1 * | 2/2004 | Heaney et al. | 435/287.2 |
| 2004/0063152 | A1 | 4/2004 | Gumbrecht et al. | |
| 2007/0148678 | A1 | 6/2007 | Ehben et al. | |
| 2010/0047132 | A1 | 2/2010 | Tajima | |

FOREIGN PATENT DOCUMENTS

| | | |
|---|---|---|
| DE | 3733098 | 4/1988 |
| DE | 196 46 505 | 5/1998 |
| DE | 199 16 867 | 10/2000 |

(Continued)

OTHER PUBLICATIONS

Notification of Reason for Refusal for corresponding Japanese patent application No. 2011-510959 mailed on Aug. 7, 2012 (with English translation).

*Primary Examiner* — Betty Forman
(74) *Attorney, Agent, or Firm* — Harness, Dickey & Pierce, P.L.C.

(57) ABSTRACT

A titer plate and a method for detecting an analyte, and the use thereof are disclosed. According to at least one embodiment of the invention, it is proposed that a plurality of depressions and a biochip of the titer plate sposed adjacent thereto be surrounded by a wall in order to effectively prevent sample contamination when there is a high degree of spatial integration.

12 Claims, 4 Drawing Sheets

FOREIGN PATENT DOCUMENTS

| | | | |
|---|---|---|---|
| DE | 100 58 397 | A1 | 6/2002 |
| DE | 101 26 341 | A1 | 12/2002 |
| DE | 102 33 212 | A1 | 2/2004 |
| DE | 10 2005 059535 | A1 | 6/2007 |
| EP | 1780290 | | 5/2007 |
| EP | 2 000 808 | A1 | 12/2008 |
| JP | 62-069139 | | 3/1987 |
| JP | 2003-262574 | | 9/2003 |
| JP | 2005-532043 | | 10/2005 |
| WO | WO-99/07879 | A1 | 2/1999 |
| WO | WO-03/087410 | A1 | 10/2003 |
| WO | WO-2007/076023 | A2 | 7/2007 |
| WO | WO-2007111347 | A1 | 10/2007 |
| WO | WO 2008/061165 | | 5/2008 |

* cited by examiner

TITER PLATE, READING DEVICE THEREFOR AND METHOD FOR DETECTING AN ANALYTE, AND USE THEREOF

PRIORITY STATEMENT

This application is the national phase under 35 U.S.C. §371 of PCT International Application No. PCT/EP2009/056231 which has an International filing date of May 22, 2009, which designates the United States of America, and which claims priority on German patent application number DE 10 2008 025 992.6 filed May 30, 2008, the entire contents of each of which are hereby incorporated herein by reference.

FIELD

At least one embodiment of the present invention generally relates to a titer plate for detecting an analyte and/or to a reading device therefor. In addition, at least one embodiment of the invention generally relates to a method for detecting an analyte. Furthermore, at least one embodiment of the present invention generally covers the use of such methods, titer plates, and a combination of titer plate and reading device.

BACKGROUND

Molecular diagnostic analyses are used for determining, for example, viral loads of HI viruses, hepatitis C and hepatitis B viruses. In a central laboratory, such analyses are nowadays often carried out on liquid-handling robotic systems. The reaction vessels used are microtiter plates, in particular 96-well plates having, for example, 8 rows of 12 wells. These wells are arranged at standardized intervals of about 0.9 cm from one another. Sample material and reagents are pipetted into predetermined wells of the titer plates by the liquid-handling robot in a freely programmable manner by means of pipet tips made of plastic or washable, reusable tips. Also, some processing steps, such as incubation at a certain temperature, mixing processes, or, for example, magnetic separation processes, are carried out in the liquid-handling robotic system.

A virtually indispensable method in molecular diagnostics is an amplification of a target—of the analyte—by a thermal cycling reaction, such as in a polymerase chain reaction (PCR) for example. Very small, only indirectly detectable amounts of analyte molecules are exponentially multiplied to detectable amounts.

A manipulation of samples which are to be amplified or which are amplified is extremely critical. Very small contaminations, via an aerosol formation for example, having, if present, even only single molecules would lead to sample material having false-positive or increased quantitative results. Therefore, it is customary in molecular diagnostics to carry out sample preparation and amplification in separate rooms. This is, however, very laborious and requires the handling of the samples by laboratory personnel.

An approach consists in a hermetic sealing of the titer plate with laminating film before carrying out the PCR, as described in DE 10 2005 059 535 A1. The titer plate must then no longer be opened in the same room. This measure of having separate rooms is contrary to the trend of integrating and automating analytical processes.

In order to analyze the resulting PCR product comprising the amplified analyte, optical methods based on real-time PCR are, for example, a possibility. There are, however, measurement methods in molecular diagnostics for electrical detection, with hybridization reactions being carried out in the methods. A method according to this type is known from WO 99/07879 A1. For this purpose, the resulting PCR product is transferred from the reaction vessel to a further vessel for the hybridization. A solution for a contamination-free transfer is in a hermetic integration of the vessels for the PCR and the hybridization in one closed cassette, such as, for example, in a quicklab® point-of-care cassette. This solution is, however, often too expensive for a routine, multifarious use and allows only comparatively low throughputs.

For an efficient detection, a product of the hybridization reaction with the amplified analyte can be electrically recorded. The quicklab® mentioned exemplarily is disclosed, for example, in DE 102 33 212 A1. A further arrangement for a biochip is known from DE 100 58 397 A1. DE 101 26 341 A1 teaches a biochip which, through hybridization with an analyte, changes an electrically recordable property.

SUMMARY

At least one embodiment of the present invention provides a titer plate which makes possible an improved automated handling of the amplified samples.

The titer plate according to at least one embodiment of the invention preferably has wells which are arranged in intervals which correspond to the intervals in a standard microtiter plate so that the titer plate according to at least one embodiment of the invention can be handled by a liquid-handling robot. This standard interval is, for example, 9 mm. Furthermore, the titer plate preferably has the length and the width of a standard titer plate; for example, it preferably corresponds to the standard titer plate format having 12×8 wells. The thickness of the titer plate according to the invention is preferably greater in order to accommodate the wall which surrounds each set of one biochip and multiple wells, as described in more detail further below.

The titer plate according to at least one embodiment of the invention can preferably be handled by a liquid-handling robot which has a supply of fresh pipet tips at its disposal. It can grip these tips, move to any one of the, for example, 12×8=96 positions of the wells on a standard titer plate, lower them there, and aspirate or inject liquid from/into the well. Furthermore, it can deposit a used pipet tip in a waste container, grip a new, clean pipet tip, and continue processing with this tip.

For the detection of the analyte, at least one biochip is, according to the invention, arranged on the titer plate. "Biochip" is understood to mean a chip which is suitable for detecting an analyte, a certain DNA for example, and, in particular, generates an electrical signal in the presence of the analyte. Typically, the biochip has one or more sensitive surfaces having capture molecules which each bind specifically to one analyte. On one biochip, there can be arranged multiple sensitive surfaces having different capture molecules, for example, from 8 to 400, particularly preferably 64 or 128, sensitive surfaces or spots. The biochip is, for example, a CMOS chip having universal Zip code capturers. Preferably, multiple biochips are present on a titer plate, in particular from 6 to 24, preferably 12 biochips, so that, for example, 12 random access multiplex assays can be carried out.

When analyte molecules attach to the capture molecules, for example hybridize with them, a change in the capacitance at the sensitive surface, for example, is effected, which can be read electrically. This preferably occurs as follows: the analyte or the target is biotinylated. After analyte molecules have bound to the capture molecules, a labeling enzyme, such as, for example, streptavidin or AG phosphatase, is added. This enzyme binds to the biotin of the target. When a substrate is subsequently added, this results in a reaction product which generates an electrical signal which can be read from the biochip. Particularly preferably, the biochip is designed for detecting DNA by means of hybridization to suitable capture molecules.

Preferably, the sensitive surface(s) of the biochip is/are arranged on one side, preferably the upper side, of the biochip, whereas the contacts at which the electrical signal can be read are arranged on an opposite side of the biochip. Preferably, from 5 to 100, in particular from 8 to 12, sensitive surfaces, and the same number of contacts, are arranged on one biochip so that multiple different analytes can be simultaneously tested.

The biochip is preferably embedded into the titer plate; for example, the biochip is set into a plastic ring which, in turn, is inserted into an appropriate indentation of the titer plate so that sample material or reaction material can be contacted with the preferably upwardly pointing sensitive surfaces of the biochip. Preferably, the biochip is provided with a seal on the side of the sensitive surfaces—for example, upwardly facing—with the seal preventing contaminants from being able to reach the capture molecules. The seal is, for example, a cover made of an elastomeric and/or thermoplastic material.

The biochip preferably spans an area on which, in a standard titer plate, a fixed number of wells is arranged, such as, for example, 2, 4, 6, or 8 wells. At the standard position of a well, a liquid-handling robot can stop and suck in or deliver material. As a result, the biochip can be filled with sample material, reaction material or with labeling enzymes and substrate by liquid-handling robots.

Next to each DNA chip, there are arranged in each case multiple wells or cavities in which, for example, an amplification of the target can be carried out, by way of a PCR reaction for example, or in which other reagents are provided. Thus, each set of one biochip and multiple wells forms one unit in which a particular analysis is carried out. This unit is enclosed by a wall. In the unit, all necessary steps for the detection can be carried out. Owing to the spatial separation of the units, many units can be accommodated on a very small surface without risking the contamination of the individual samples. A massively parallel study of very many samples is fast and cost-effectively possible.

A unit surrounded by a wall includes, for example, 2, 4, 6, 8, or 10 wells and one, two, or three biochips. Particularly preferably, 4 wells and 1 biochip form one unit, with the biochip occupying an area which, in a standard titer plate, is likewise occupied by 4 wells. A preferred unit thus corresponds to 8 wells and thus has 8 positions in which a liquid-handling robot can handle a pipet tip. A titer plate in the standard 12×8 format thus has 12 units which are each separated from one another by a wall.

The titer plate according to at least one embodiment of the invention is, for example, a block having a height of about 20-70 mm, preferably of 45±10 mm, with the wall between the individual units being formed as a result of each unit being arranged in a type of recess in the block. The wells and the biochip are arranged at the base of the recess. The liquid-handling robot can, within the recess, move a pipet tip from one well to the next well or to the biochip. The wall which surrounds the biochip and multiple wells is the wall of the recess and is preferably about as tall as the height of the titer plate, i.e., preferably about 20-70 mm, with preference 45±10 mm. As a result, there is effective prevention of single drops of one unit being able to reach an adjacent unit during pipetting. Thus, the titer plate preferably has as many recesses as units, each unit comprising multiple wells and one biochip.

Such a recess is preferably only open toward a first side, preferably the upper side, of the titer plate. A pipet can be introduced into each unit via the recess and remains during the transfer of the sample, for example, from one well to the biochip within the enclosed space of the unit. The side opposite to the first side, preferably the bottom side, of the titer plate provides a slot for the biochip and is provided with curvatures which each correspond to a well.

Particularly preferably, the recesses are each formed in the shape of an elongated hole and have, for example, an approximate "E" shape for each unit. The recesses are adapted to the sequence of movement of a liquid-handling robot. The elongated hole spans all four wells and at least one position above the biochip. It effectively forms a single line of connection between the wells and the biochip. This has the advantage that walls are arranged not only between the individual units but also, in part, between the individual wells within a unit. Once a pipet tip comes into contact with sample material, the tip can be kept within this unit. In contrast to known titer plates, very small droplets cannot get into other analysis units and contaminate them, since a used pipet tip is not lead out via other wells or chips. The recess is, according to a development, formed such that one or more pipet tips can remain therein.

The titer plate is preferably made of plastic. Since it is preferably provided with recesses which are open toward one side, it is possible to produce the titer plate (without biochips) in an injection-molding process. Preferably, the walls or recesses and the wells are manufactured as a single plastic injection-molded part into which the biochips are later embedded. Alternatively, the titer plate can also be formed as a flat plate with wells and slots for the biochips, with wall elements being placed on the plate between the individual units. Since, in this case, a seal between the wall elements and the plate has to be provided, this embodiment is, however, not preferred.

The biochip is preferably embedded into the titer plate such that each corner of the biochip is at the corresponding position of a well on the microtiter plate in standard format. At at least one of these positions, a filling port is present in an elastomeric cover or seal of the biochip. The elastomeric seal serves to protect the sensitive surfaces of the biochip from contamination. In, for example, a two-component injection-molding process during the production of the titer plate, the seal can be integrated into this plate. Alternatively, the seal or cover is stretched by a plastic ring into which the biochip is set. Particularly preferably, the elastomeric seal is easily spaced from the sensitive surface of the biochip, whereby a biochip chamber is formed in between and is connected by liquid with the sensitive surfaces of the biochip.

Liquid can preferably be injected into the biochip chamber via the filling port, and the liquid then gets into contact with the capture molecules and is thus analyzed by the biochip. Since the filling port of the biochip effectively "aligns" with one of the standard positions of the wells of a titer plate, a pipet can automatically transfer a sample to the biochip by means of the liquid-handling robot.

Particular preference is given to providing, above the elastomeric seal of the biochip, at least one and preferably two deposit positions for a pipet tip, specifically at one or preferably two of the, for example, 4 positions which each correspond to a well on a standard titer plate and are thus accessible to a liquid-handling robot. A pipet which has come into contact with sample material can be deposited at this site and thus remain within the unit, even when, if necessary, fresh pipet tips are used in the unit. Furthermore, a further 4 pipet tips can remain at the positions of the 4 wells.

Further preference is given to providing an overflow reservoir for each unit to collect excess liquid. In a preferred embodiment, the overflow reservoir is directly connected or connectable with the biochip chamber. Thus, liquid which is filled into the biochip chamber flows directly further into the overflow reservoir. Since the biochip is preferably set into the base of the titer plate, the overflow reservoir is preferably located above the biochip chamber. Therefore, the overflow reservoir is preferably provided with a wick or another absorbent material which draws the liquid from the chip chamber. In this way, all liquid which is pushed through the chip chamber is collected by the overflow reservoir. The overflow reservoir holds preferably from 0.5 ml to 5 ml, particularly preferably 1-2 ml. The overflow reservoir is further preferably provided with an overflow wall which prevents a backflow of liquid into the biochip chamber. Alternatively, the overflow reservoir could also be filled through, for example, an inlet at one of the standard positions which correspond to the wells on a standard titer plate.

According to an alternative embodiment, the invention comprises a titer plate for detecting an analyte, having at least one biochip, wherein the at least one biochip is designed for detecting an analyte and is surrounded by a wall, wherein a seal, preferably an elastomeric seal, is applied on the at least one biochip (14), which seal, together with the biochip, defines a biochip chamber and, with an overflow reservoir, is directly connected or connectable with the biochip chamber. Thus, liquid which is filled into the biochip chamber flows directly further into the overflow reservoir. Since the biochip is preferably set into the base of the titer plate, the overflow reservoir is preferably located above the biochip chamber. Therefore, the overflow reservoir is preferably provided with a wick or another absorbent material which pulls the liquid from the chip chamber. In this way, all liquid which is pushed through the chip chamber is collected by the overflow reservoir. According to this alternative embodiment, no further wells in the titer plate are necessary, and the entire base surface of the titer plate can therefore be completely occupied by biochips.

All further preferred inventive features which are mentioned in connection with the first embodiment of the invention according to claim 1 can also be provided in the alternative embodiment of the titer plate according to the invention.

Optionally, the titer plate according to at least one embodiment of the invention can be penetrated by at least one hole. This hole runs across the support material of the titer plate and preferably runs between the wells and the biochip. A reduced pressure can be applied over it in order to aspirate any droplets of contaminants from the space above the titer plate. Preferably, each unit or recess is provided with its own hole.

In addition, at least one embodiment of the invention provides a reading device for a titer plate, said device being designed to ensure a further improvement in the automated handling of the samples. The reading device provides at least one electrical contact surface or readout surface for the biochip. Preferably, the readout surface is heatable, since the readout result of the biochip is generally readable only after appropriate heat treatment.

The reading device comprises, in addition, depressions for the wells, the depressions being preferably conceived as heatable slots (thermoblocks). When placing the titer plate on the reading device, each well is accommodated in a depression; preferably, the well is very tightly surrounded by the depression in order to ensure a good heat transfer. Preferably, each set of depressions corresponding to the wells formed in a unit forms an independent thermal cycle unit, hereinafter also referred to as a thermoblock. Through appropriate heating of the depressions, it is possible to carry out, for example, a PCR in the wells.

Preferably, a reading device has units which each comprise four depressions and one contact surface and which are independent of one another.

In a further embodiment of the present invention, an improved method is provided for detecting an analyte by means of a biochip. By using a titer plate according to at least one embodiment of the invention, liquid handling can be carried out by means of liquid-handling robots.

The method comprises, in addition to an introduction of the sample into one of the wells of the titer plate, preferably an amplification of the analyte and provides the advantage of a spatial integration of a hybridization area of the biochip in one common space. A contamination by other sample materials is effectively avoided, since the pipet tip remains in this space.

According to a preferred embodiment of the method, the liquid-handling robot can, for each unit, use multiple pipet tips which each remain within the unit after use. This has the advantage that neighboring units cannot be contaminated with amplified material when the pipet tip is transported away over them. Particularly preferably, used pipet tips are deposited on the deposit positions on the cover or seal of the biochip.

By way of example, not only one but multiple samples, from various tissues of the same patient for example, are introduced into the different wells of a unit. After a PCR, the reaction mixes can be successively transferred with different pipet tips from the different wells into the biochip chamber, and the biochip can be read. The pipet tip is completely emptied over the biochip chamber, with excess liquid flowing into the overflow reservoir. Afterwards, the pipet tip is preferably deposited on the same well from which the PCR reaction mix was transferred. For further manipulations, use is made of a fresh pipet tip which, in turn, remains in the unit or recess.

Preferably, after the transfer of the PCR reaction product, a further liquid, in particular a labeling liquid, is transferred with a pipet tip onto the biochip or into the biochip chamber. The label is, for example, streptavidin or AG phosphatase, which binds to the biotinylated analyte. The pipet tip with which the label was transferred remains unemptied, since it, if necessary, is used again for further samples, and is therefore parked on one of the deposit or park positions.

Subsequently, with one further pipet tip, a substrate is preferably pipetted into the biochip chamber. This substrate forms a reaction product which induces an electrical signal on the biochip. The pipet tip with which the substrate was transferred remains unemptied, since it, if necessary, is used again for further samples, and is therefore parked on a second deposit or park position.

Thus, a feature of the preferred method is multiple pipet tips remaining within the recess, for example, on different deposit positions or in the wells.

For the amplification of the analyte, a thermal cycling reaction is preferably used. According to a development of the method according to at least one embodiment of the invention, a polymerase chain reaction (PCR), an allele-specific primer expression (ASPE), and/or an amplification refractory mutation system (ARMS) come into consideration.

In addition to a temperature-controlled amplification of the analyte, a temperature-controlled hybridization by way of the biochip is also provided here.

An improved detection of the analyte is, in addition, achieved by a temperature-controlled electrical, in particular electrochemical, detection.

In addition, to improve the automated handling of the samples, an analysis instrument comprised of a combination of reading device and titer plate is provided. This combination is adapted to commercially available liquid-handling robots.

A further aspect of at least one embodiment of the present invention relates to the use of the titer plate according to at least one embodiment of the invention. The wells of a unit can be used with four different comparative concentrations for quantitative determinations. This is conceivable for expression experiments in integrated DNA technology or multiple multiplexing in the case of single nucleotide polymorphisms (SNP).

BRIEF DESCRIPTION OF THE DRAWINGS

With reference to the accompanying drawings, preferred example embodiments of the invention will now be described.

In the drawings.

DETAILED DESCRIPTION OF THE EXAMPLE EMBODIMENTS

The example embodiments of the present invention will be described below with reference to the drawings.

Figure 1:
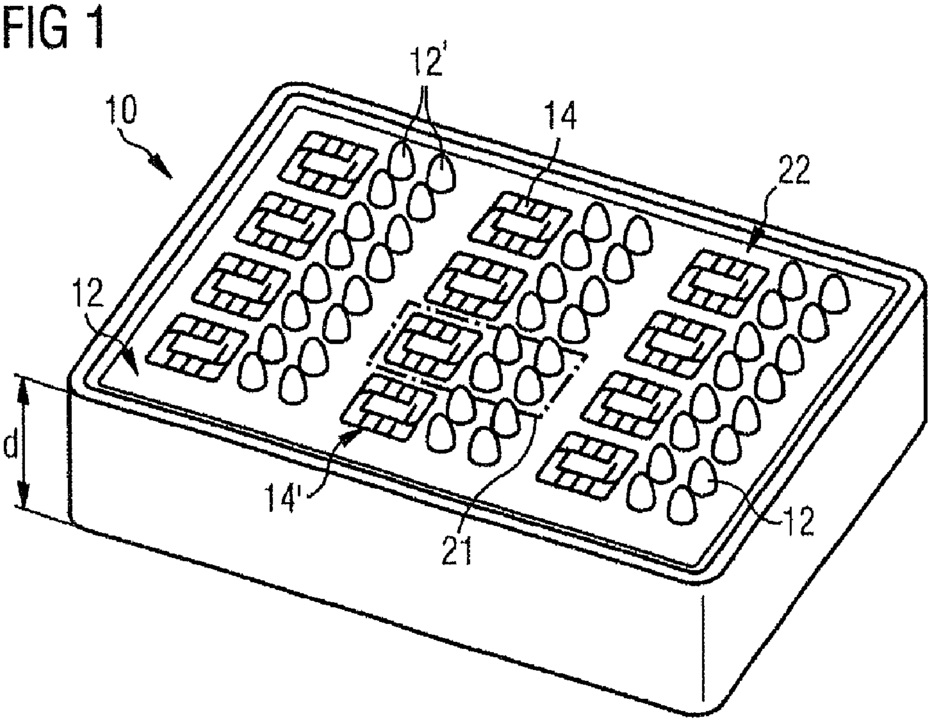
FIG. 1 shows a perspective view of an example embodiment of a titer plate according to the invention.

FIG. 1 shows a titer plate 10 for detecting an analyte from the bottom side 22. The titer plate 10 has multiple wells 12 arranged in rows, the wells being visible from the bottom side 22 as curvatures 12'. The wells 12 are spaced from another and aligned to one another such that a liquid-handling robot having a pipet tip can introduce necessary reagents, solvents, and/or a sample to be tested for the analyte into the wells 12.

Next to every two rows of wells 12, there is arranged a row of biochips 14. The biochips 14 are likewise positioned in relation to the wells 12 such that the robot can move the pipet tip there automatically in a program-controlled manner. These biochips 14 are, for example, designed to detect a DNA by means of hybridization, with at least one electrical property of the biochip 14 changing. Such biochips 14 can, if necessary, also include a smart card laboratory.

The titer plate 10 has a modular structure; it comprises a block, an injection-molded part for example, made of plastic, in which the wells 12 or curvatures 12' are shaped, and the biochips 14. These biochips are accommodated in the block in slots 14'. Below the biochips 14, there is preferably arranged a seal which is made of a thermoplastic elastomer and which seals the slot 14' toward the upper side of the titer plate (lying underneath in FIG. 1). In the seal, there are preferably arranged funnel-shaped openings which form an inlet port, an outlet, and, if required, deposit positions. Furthermore, the biochips 14 can each be set into a plastic ring which is affixed in the slot 14', for example, glued on or welded.

In order to be able to test multiple samples on one titer plate 10, multiple—here, four—wells 12 having a biochip 14 each are, in each case, combined to form a unit 21, which is encircled by a dashed-and-dotted line in FIG. 1. At least along this line 21, there runs a wall 16 which encloses four wells 12 and one biochip 14 and protects them from contamination. For this purpose, the injection-molded part has a thickness d—i.e., a wall height—of from about 50 mm to about 60 mm. The titer plate 10 has 16 of these units 21.

Figure 2:
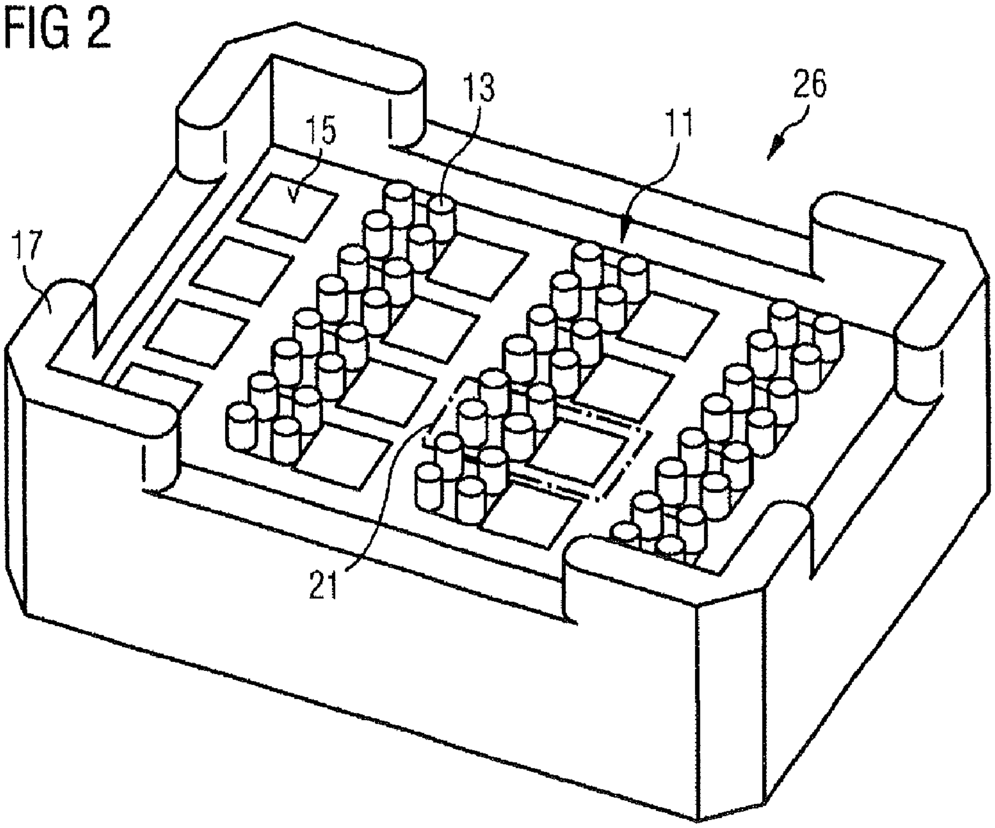
FIG. 2 shows a perspective view of an example embodiment of a reading device according to the invention for a titer plate.

FIG. 2 shows an example embodiment of a reading device for a titer plate 10. On the reading device 26, firstly, there are arranged a row of depressions 13 which serve as heatable slots for the wells 12 of the titer plate. In particular, the curvatures 12' shown in FIG. 1 fit into the depressions 13. The four depressions 13 of a unit 21 are, in each case, combined to form a thermoblock 11 and are heatable, preferably independently of one another and, in particular, of the other thermoblocks 11. The reading device 26 depicted thus comprises 12 independent 4-well thermoblocks 11. With a thermoblock 11, an analyte in the wells 12 can be multiplied by means of an amplification reaction to an easily detectable amount.

The reading device 26 provides, in addition, some electrical readout surfaces or contact surfaces 15 for the biochips 14. Each biochip 14 lies on top of a readout surface 15 so that the corresponding contacts on the biochip 14 are contacted and read. Preferably, the temperature of the readout surfaces 15 can be controlled. On a readout surface 15, there are arranged 8 electrical contacts for example.

The contact surfaces 15 and depressions 13 are surrounded by a border 17 which can align and hold a titer plate 10 shown in FIG. 1 on the reading device 26.

The base surface and height of the reading device 26 is preferably compatible with the known STARlet® system; the dimensions are thus, for example, 150×110×110 $mm^3$ and fit into a 7-track carrier. The reading device 26 preferably comprises 12 independent 4-well thermoblocks or thermocyclers 11, with which any programmable PCR can be carried out, and also 12 independent temperature-controlled electrical biochip readout blocks. The integrated electronics preferably comprise a communication interface, 24 independent temperature-control units, and also 12 independent digital interfaces for the biochip readout.

Figure 3:
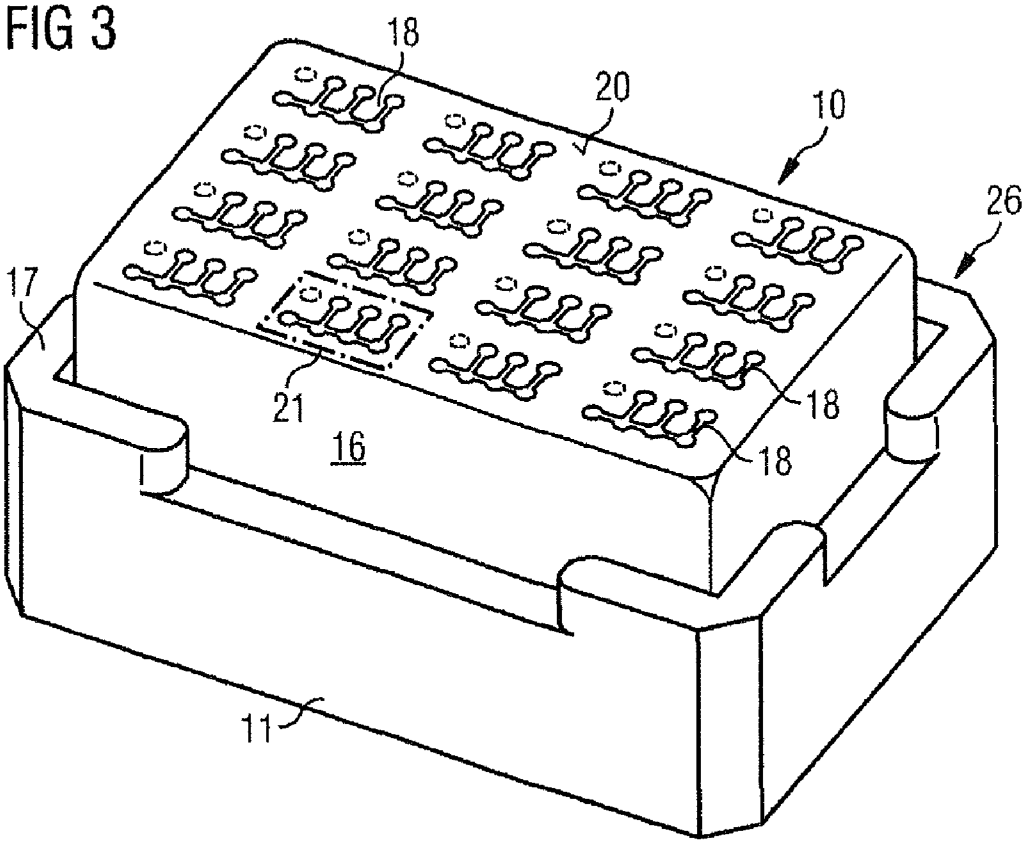
FIG. 3 shows a perspective view of a combination of a titer plate according to FIG. 1 with a reading device according to FIG. 2.

FIG. 3 shows the titer plate 10 of FIG. 1 from the upper side, placed onto a reading device 26 according to FIG. 2. The titer plate 10 is supported by the border 17. On the upper side 20 of the titer plate 10, 16 recesses 18 are visible, each having the shape of an approximately E-shaped elongated hole. The recesses 18 pass through to the base of the titer plate 10, i.e., are as if "milled" into a block. Each recess 18 is therefore bordered by relatively thick walls 16 which stretch to the wells 12 in the titer plate 10. The walls 16 provide an enclosure for the individual units comprised of wells 12 and the biochip 14. These units are arranged at the base 19 of the recess 18 and are accessible by means of liquid-handling robots. The liquid-handling robot moves a pipet tip 40 along the elongated hole 18 to transfer an amplified sample mixture from the well 12 into the biochip 14.

Figure 4:
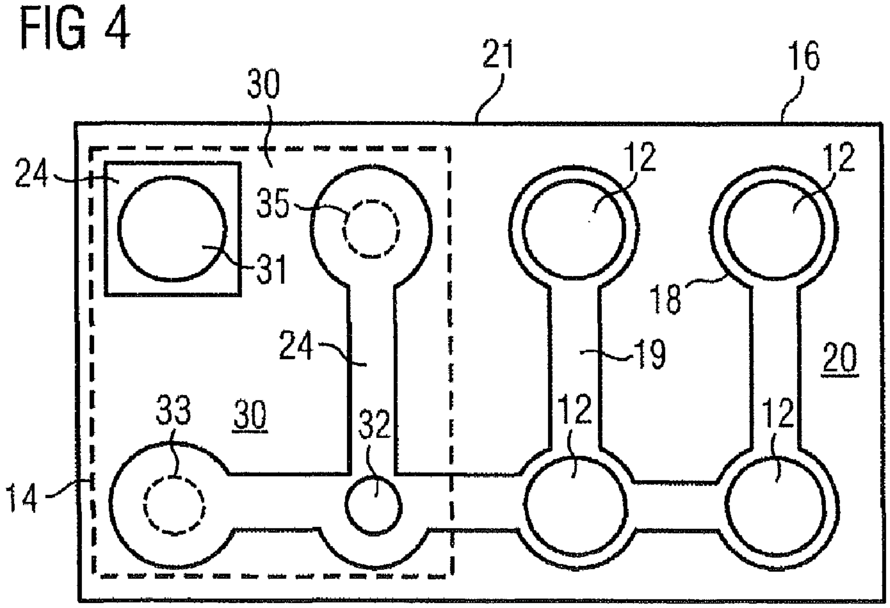
FIG. 4 shows a top view of a section of the upper side of the titer plate according to an embodiment of the invention.

FIG. 4 depicts schematically a top view of an individual unit 21—comprising a biochip and four wells—of a titer plate 10 from the upper side 20. A recess 18 is introduced into the titer plate 10. The recess 18 is formed as an elongated hole and enclosed by the walls 16. The recess 18 is open toward the upper side 20.

The base 19 of the titer plate 10, in which base four wells 12 shown on the right are set, is seen through the recess 18. On the left-hand side, the biochip 14 is below the dotted line. The biochip 14 is, for example, covered by a seal 30 in which there is set, at 32, a filling port through which a sample can be contacted with the biochip 14 by means of a pipet tip. At positions 33 and 35, the seal 30 on the biochip 14 is not permeable but is provided with a small slot for a pipet tip. This slot can, for example, be a small indentation in the seal 30, in which a pipet tip can be accommodated. Such indentations are, however, not absolutely necessary. In any case, a pipet tip can be deposited at positions 33 and 35. Therefore, these positions 33, 35 are also connected with the elongated hole 18. The opening of the pipet tip is sealed by the elastomeric material of the seal 30 so that the pipet tip can still be filled with, for example, substrate or labeling enzyme when it is parked at one of these deposit positions 33 or 35. At position 24, there is arranged an opening to an overflow reservoir. This position is not connected with the elongated hole 18, since it is not necessary to move a pipet tip to this position.

For the handling of a sample in the wells 12, the recess 18 is designed in the shape of a multibranched elongated hole, which, inter alia, makes the four wells accessible effectively "from above". This means that pipet tips 40 can be introduced and moved via the elongated hole 18 by way of a liquid-handling robot. The introduced pipet tip reaches all wells 12 and also the biochip 14 without having to leave the recess 18. An amplified sample comprising the target can be picked up from one of the wells 12 by the pipet and transferred into the biochip 14 via the filling port 32. The filling port 32 penetrates the elastomeric seal or lining 30, which is applied on the biochip 14 for protection.

The liquid sample flows, via the filling port 32, from a pipet tip 40 into a biochip chamber 36 which is arranged adjacently to the sensitive surfaces of the biochip 14 and runs, in particular, between biochip 14 and seal 30. An overflow reservoir 24, which is open toward the upper side, branches off from the biochip chamber 36. In the overflow reservoir 24, there is arranged a wick element 31, in this case a cylindrical piece of absorbent material, for example, foam or absorbent cotton. The liquid sample from a pipet tip 40 thus flows further from the biochip chamber 36 into the overflow reservoir 24.

A pipet tip can, after use, remain within the recess 18 at 6 different positions: when the pipet tip is still filled with, for example, label or substrate, in particular with a liquid which will be needed again later, it can be parked on one of the two deposit positions 33, 35, where its opening is sealed by the seal 30. An empty, used pipet tip, for example, after the pipetting of PCR product from one of the wells 12 into the biochip chamber 36 via the filling port 32, can be deposited in the respective well 12. After the transfer of PCR product into the biochip chamber 36, the pipet tip can be completely emptied, since the biochip chamber 36 is directly connected with the overflow reservoir 24, into which all excess liquid is drawn off.

Figure 5:
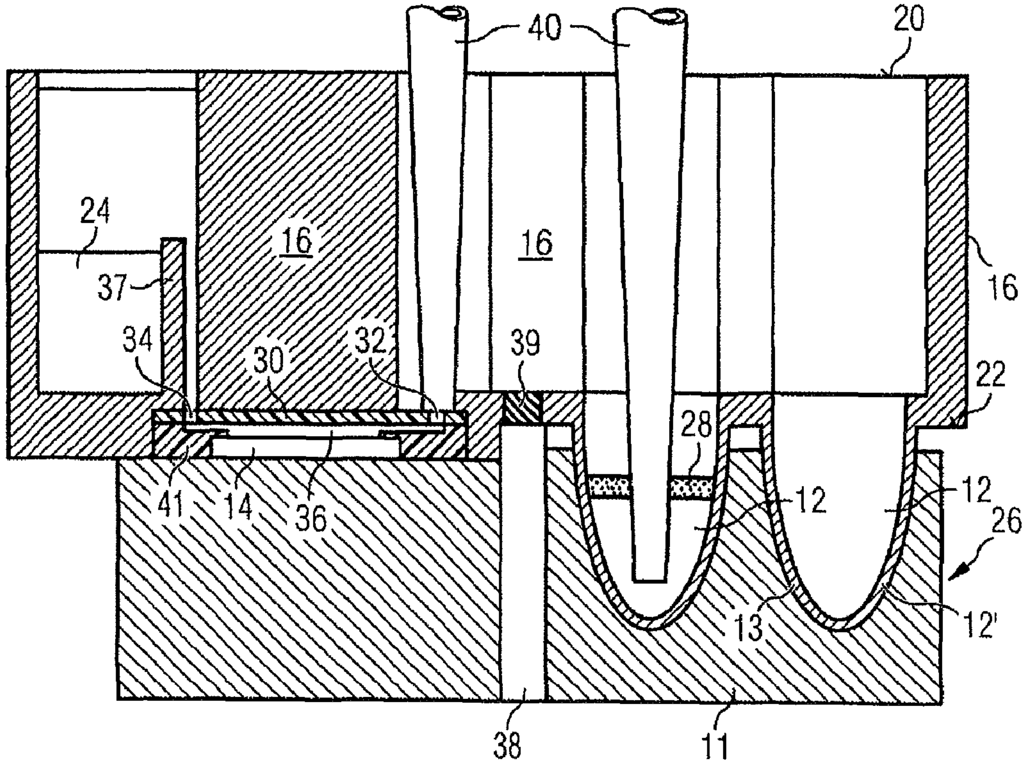
FIG. 5 shows a longitudinal section through a section of a titer plate and of a reading instrument according to a second embodiment.

FIG. 5 shows the longitudinal section of a combination of a titer plate 10 with a reading device 26, with again only one unit 21 being depicted. The titer plate 10 comprises multiple wells 12, whose curvatures 12' are introduced into depressions 13 of a thermoblock 11. The introduced sample material is replicated multiple times by means of a thermal cycling reaction, such as a PCR. In order to avoid a contamination by sample material from other wells 12, a blocking medium 28—here, a mineral oil film—is provided in one of the wells 12. Joined to the wells 12 are walls 16 which are open to the first side 20. Thus, pipet tips 40 introduced by a liquid-handling robot can access the wells 12. Between the two wells 12 and the left well 12 and the biochip 14, the wall 16 is, in each case, not cut, but visible in top view.

The biochip 14 is bordered by a plastic ring 41 which preferably has a sealing lip and seals the biochip 14 against the titer plate 10 or the seal 30. The biochip 14 has, toward the top, a seal 30, made of polypropylene for example, as contamination protection. Between the seal 30 and the surface having capture molecules for the analyte on the biochip 14, there is formed a biochip chamber 36 into which a sample can be collected. The amplified sample can be transferred into the biochip chamber 36 via a filling port 32 with the pipet tip 40 without leaving the enclosed recess 18.

A hole 38 is arranged between the wells 12 and the filling port 32. This hole 38 penetrates the entire titer plate 10. By applying a reduced pressure or vacuum, it is possible to generate a steady air flow which further reduces the likelihood of a contamination with sample material. The air flow enters the titer plate 10 via the first side 20. An aerosol, droplets, or the like is then carried away with the air flow via the hole 38. There is thus provided an extraction system for the titer plate 10 according to an embodiment of the invention. The hole 38 can, in addition, be overlaid with a filter material 39.

The sample enters the chip chamber 36 above the biochip 14 via the filling port 32. If too much liquid is filled into the biochip chamber 36, this liquid flows into an overflow reservoir 24 via the outlet 34 in the seal 30. So that liquid already present in the overflow reservoir 24 cannot flow back, an interior wall 37 is provided as overflow protection, as shown in FIG. 5. In the interspace between the interior wall 37 and the wall 16, there is located, for example, an absorbing wick which can soak up excess sample liquid and conduct this liquid, by way of capillary forces, into the overflow reservoir 24, which can accommodate about 1.3 ml of liquid.

According to another embodiment which is not depicted, the overflow reservoir 24 is arranged directly above the outlet 34, but separated from the biochip chamber 36 via a gap. The overflow reservoir 24 is almost completely occupied with a wick element, as depicted in FIG. 4, which can hold about 1-2 ml of liquid. Liquid emerging at the outlet 34 is soaked up by the wick. Owing to the gap, the liquid flow immediately breaks down when no more liquid is delivered. In this way, a return flow does not occur, not even by capillary forces.

With the titer plate 10, the method according to an embodiment of the invention for detecting an analyte can be carried out by way of a biochip 14. The biochip 14 is integrated into a titer plate 10, as described above. The method comprises the following steps: an introduction of a sample into one of the wells 12 of the titer plate 10 and an introduction of reagents into the wells 12. Subsequently, an amplification reaction is carried out with the sample with reagents added, with a PCR reaction, an ASPE reaction, and/or an ARMS reaction coming into consideration. Afterwards, the resulting reaction mix is transferred onto the biochip 14, and the biochip 14, which changes at least one electrically recordable property owing to hybridization with the analyte, is read. A feature of the method according to an embodiment of the invention is that the liquids are transferred with the pipet tip 40 by way of a liquid-handling robot and that the pipet tip 40 remains within the enclosed space 18. For this purpose, it is deposited in one of the wells 12 or on one of the deposit positions 33, 35.

Owing to the use of liquid-handling robots, the analysis method becomes considerably accelerated, is less error-prone and, in addition, more cost-effective. In particular, the use thereof for quantitative determinations, an integrated DNA technology (IDT), or a multiple multiplexing in the context of SNPs becomes possible.

Figure 6:
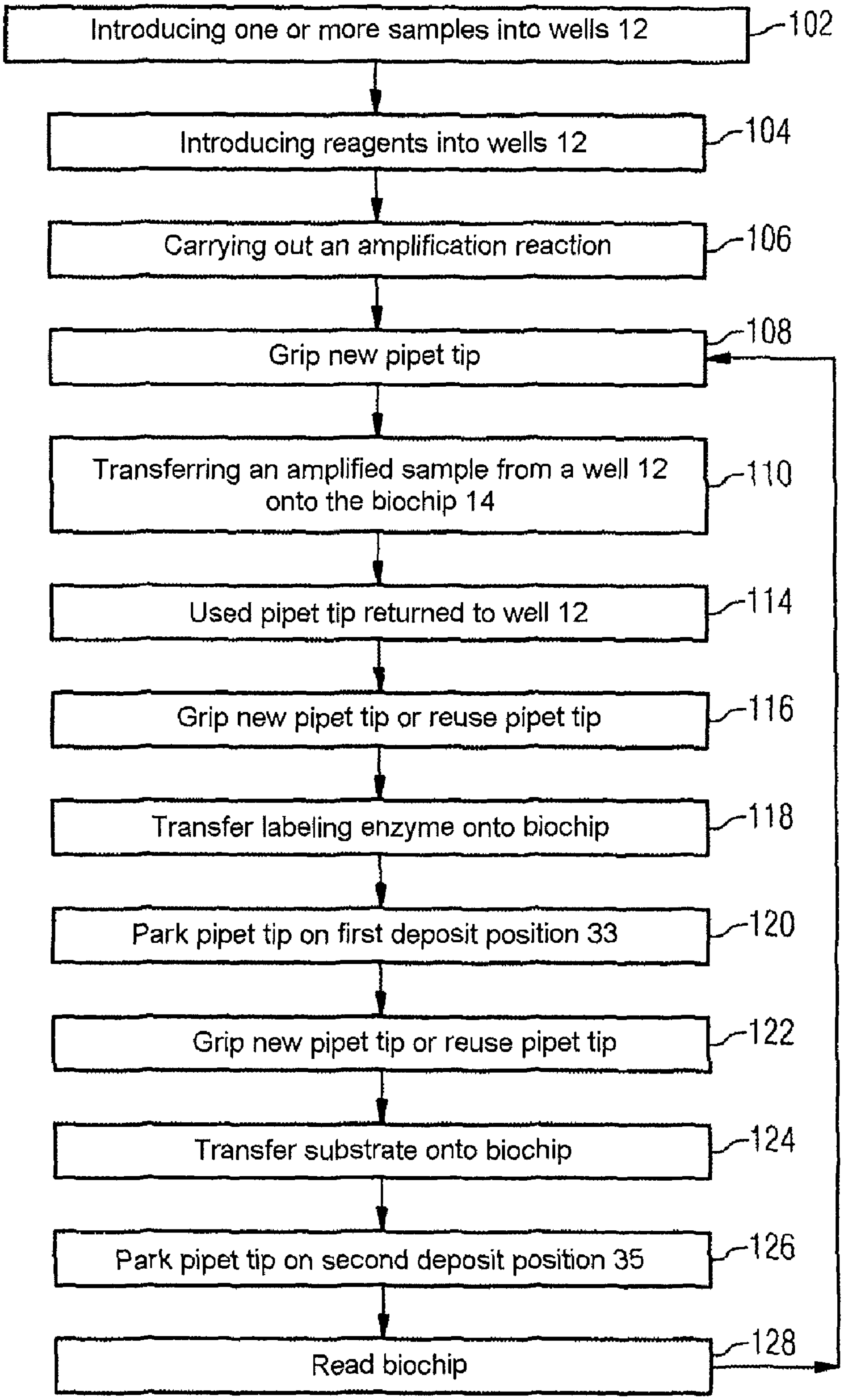
FIG. 6 shows a flowchart of a method according to an embodiment of the invention.

A method according to an embodiment of the invention for detecting an analyte by way of biochip 14 is depicted as a flowchart in FIG. 6. It initially comprises the introduction 102 of one or more sample(s) to be tested into one or more of the wells 12 of a titer plate 10. This titer plate 10 is preferably a titer plate 10 according to an embodiment of the invention, as described above. The pipet tip 40 contacted with the sample can then be disposed of in the usual way by a liquid-handling robot.

In a further procedural step 104, the reagents required for an amplification reaction of the analyte are introduced into the wells 12. For this purpose, a further pipet tip 40 is introduced into the recess 18 by the liquid-handling robot and preferably then disposed of outside the recess in the usual way. Optionally, the sample can be overlaid with mineral oil prior to the amplification reaction. After bringing together the reagents and the sample, a temperature program 106 is carried out in order to allow a PCR reaction to proceed. The reaction mix then comprises the analyte in a massively replicated form for improved detection.

The liquid-handling robot then picks up a new, clean pipet tip 40, step 108. With this pipet tip, in step 110, the reaction mix having the amplified sample is transferred from a first of the wells 12 into the biochip 14. The reaction mix is allowed to flow into the biochip chamber 36. If too much reaction mix is taken up, the excess flows into the overflow reservoir 24 via the outlet 34. The used pipet tip is, after complete emptying, deposited at the first well 12, step 114, i.e., it remains within the recess 18.

Subsequently, the liquid-handling robot firstly picks up a further new clean pipet tip 40, step 116. With this pipet tip, in step 118, a labeling enzyme is collected from a storage container located outside the recess 18 and transferred into the biochip 14. The pipet tip 40 is, afterwards, still not empty and is therefore deposited at the first deposit position 33, step 120, i.e., it remains within the recess 18.

Afterwards, the liquid-handling robot picks up a further new clean pipet tip 40, step 122. With this pipet tip, in step 124, a substrate is collected from a storage container located outside the recess 18 and transferred into the biochip 14. The pipet tip 40 is, afterwards, still not empty and is therefore deposited at the second deposit position 35, step 126, i.e., it remains within the recess 18.

Afterwards, the biochip 14 can be read, step 128.

Steps 110 to 128 can be further repeated many times, specifically with the other reaction mixes from the other wells 12. The pipet tip which is used for pipetting the reaction mix from the well 12 is placed back into the respective well 12 and remains there until it is disposed of together with the titer plate 10. The pipet tips with which the labeling enzyme and substrate were transferred are reused, and then reparked at the deposit positions 33, 35.

An embodiment of the invention thus avoids disposal of used pipet tips over other recesses 18, in which other samples are tested, and thus reduces the contamination risk.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A titer plate for detecting an analyte, comprising:

a plurality of units, each unit including:

multiple wells; and a biochip, the biochip is designed to detect an analyte and is in contact with an electrical contact surface of a reading device to generate an electrical signal in the presence of the analyte, each unit being individually enclosed by a wall.

2. The titer plate as claimed in claim 1, wherein the biochip is arranged next to the wells and wherein a recess in the titer plate is bordered by the wall, and wherein the multiple wells and the biochip are each arranged at the base of the recess.

3. The titer plate as claimed in claim 2, wherein each unit is arranged in a recess in the titer plate.

4. The titer plate as claimed in claim 3, wherein each recess is open on a first side of the titer plate, and wherein an opposite side of the titer plate is provided with a slot for the biochip and is further provided with curvatures that form the bottom of the wells.

5. The titer plate as claimed in claim 2, wherein each recess is formed as an elongated hole which spans all wells in the unit and the biochip, which are enclosed by the wall.

6. The titer plate as claimed in claim 1, wherein one elastomeric seal is applied on the at least one biochip and includes one filling port.

7. The titer plate as claimed in claim 6, wherein, on the elastomeric seal of the biochip, at least one deposit position is provided for a pipet tip.

8. The titer plate as claimed in claim 1, wherein the titer plate is injection-molded.

9. The titer plate as claimed in claim 7, wherein a biochip chamber is formed between the biochip and the seal and the biochip chamber is connectable with an overflow reservoir in order to collect a liquid from the biochip chamber.

10. The titer plate as claimed in claim 9, wherein a wick element for soaking up liquid from the biochip chamber is arranged in the overflow reservoir.

11. The titer plate as claimed in claim 1, wherein a hole penetrating the titer plate is present within a recess.

12. The titer plate as claimed in claim 2, wherein the biochip is designed for detecting DNA by way of hybridization.

* * * * *